United States Patent
Mouchel La Fosse et al.

(10) Patent No.: US 9,164,009 B2
(45) Date of Patent: Oct. 20, 2015

(54) MINIATURIZED PRESSURE SENSOR

(75) Inventors: Eric Mouchel La Fosse, Tournefeuille (FR); Lionel Songeon, Tournefeuille (FR)

(73) Assignee: NANOMADE CONCEPT, Toulouse (FR)

( * ) Notice: Subject to any disclaimer, the term of this patent is extended or adjusted under 35 U.S.C. 154(b) by 194 days.

(21) Appl. No.: 13/988,355

(22) PCT Filed: Nov. 24, 2011

(86) PCT No.: PCT/EP2011/070973
§ 371 (c)(1),
(2), (4) Date: May 20, 2013

(87) PCT Pub. No.: WO2012/069604
PCT Pub. Date: May 31, 2012

(65) Prior Publication Data
US 2013/0228018 A1    Sep. 5, 2013

(30) Foreign Application Priority Data
Nov. 24, 2010 (FR) ...................... 10 59678

(51) Int. Cl.
*G01L 9/00* (2006.01)
*H01G 7/00* (2006.01)
*G01R 27/00* (2006.01)
(Continued)

(52) U.S. Cl.
CPC ............... *G01L 9/12* (2013.01); *A61B 5/02158* (2013.01); *A61B 5/6876* (2013.01); *A61B 5/6884* (2013.01); *G01L 9/0027* (2013.01); *A61B 2562/0247* (2013.01)

(58) Field of Classification Search
None
See application file for complete search history.

(56) References Cited

U.S. PATENT DOCUMENTS 5,952,040 A *  9/1999 Yadav et al. ............... 427/126.3
6,589,682 B1 *  7/2003 Fleckner et al. ............ 429/458
(Continued)

FOREIGN PATENT DOCUMENTS

| DE | 102005035022 A1 | 11/2006 |
| EP | 1635158 A2 | 3/2006 |

(Continued)

OTHER PUBLICATIONS

Mueggenburg et al., "Elastic membranes of close-packed nanoparticle arrays," Nature Materials, Sep. 1, 2007, pp. 656-660, vol. 6, No. 9.

*Primary Examiner* — Peter Macchiarolo
*Assistant Examiner* — Jermaine Jenkins
(74) *Attorney, Agent, or Firm* — IM IP Law PLLC; C. Andrew Im

(57) ABSTRACT

The invention concerns a device for measuring the pressure of a fluid carried in a conduit. The device comprises a first electrode, a second electrode, a nanoassembly of conductive or semi-conductive nanoparticles in contact with the two electrodes, and a measurement device. The measurement device provides proportional information with respect to an electrical property of the nanoassembly. The electrical property is measured between the first and second electrode, and the electrical property is sensitive to the distance between the nanoparticles of the nanoassembly. The nanoassembly is mechanically linked to a flexible substrate having a mechanical linkage with the fluid carried in the conduit such that the distances between the nanoparticles of the nanoassembly are modified by a pressure variation in the fluid.

9 Claims, 3 Drawing Sheets

(51) Int. Cl.
  *G01L 9/12* (2006.01)
  *A61B 5/0215* (2006.01)
  *A61B 5/00* (2006.01)

(56) References Cited

U.S. PATENT DOCUMENTS

| | | | | |
|---|---|---|---|---|
| 6,756,795 | B2 * | 6/2004 | Hunt et al. | 324/701 |
| 6,897,009 | B2 * | 5/2005 | Johnson et al. | 430/315 |
| 7,123,826 | B2 * | 10/2006 | Belcher | 392/478 |
| 7,385,266 | B2 * | 6/2008 | Segal et al. | 257/414 |
| 7,641,863 | B2 * | 1/2010 | Doktycz et al. | 422/503 |
| 7,844,347 | B2 * | 11/2010 | Brabec et al. | 607/121 |
| 8,106,510 | B2 * | 1/2012 | Altman et al. | 257/739 |
| 8,717,046 | B2 * | 5/2014 | Jensen et al. | 324/708 |
| 8,809,208 | B2 * | 8/2014 | Altman et al. | 438/795 |
| 8,905,659 | B2 * | 12/2014 | Jiang et al. | 400/479 |
| 2007/0074577 | A1 | 4/2007 | Cobianu et al. | |
| 2008/0161887 | A1 * | 7/2008 | Hagen | 607/72 |

FOREIGN PATENT DOCUMENTS

| | | | |
|---|---|---|---|
| EP | 2053495 | A2 * | 4/2009 |
| WO | WO-2006/122750 | A1 | 11/2006 |

* cited by examiner 5A       5B

MINIATURIZED PRESSURE SENSOR

RELATED APPLICATIONS

This application is a §371 application from PCT/EP2011/070973 filed Nov. 24, 2011, which claims priority from French Patent Application No. 10 59678 filed Nov. 24, 2010, each of which is herein incorporated by reference in its entirety.

TECHNICAL FIELD OF INVENTION

The invention concerns a miniaturized pressure sensor. It is particularly useful for measuring the pressure of a fluid carried in a conduit and more specifically for measuring a spatial, axial or circumferential distribution of this pressure in this conduit.

The measurement of the relative or absolute pressure, and more specifically of the spatial or temporal pressure distribution, of a fluid carried in a conduit makes it possible to determine many parameters relating to said fluid's flow conditions and to determine intrinsic properties of the fluid carried in the conduit, such as said fluid's viscosity or its instantaneous flow rate.

Knowing these parameters is especially useful when the carried fluid is a human or animal bodily fluid, such as blood or urine. For example, the measurement of a fluid's pressure or of the spatial distribution of this pressure during the bypassed extracorporeal circulation of this fluid in an instrumented conduit allows to collect information about the properties of the fluid and its conditions of circulation, without taking samples of the fluid. According to another example of application, particularly advantageous, the pressure, or its spatial or temporal distribution, can be measured on an intracorporeal conduit, such as a blood vessel.

BACKGROUND OF THE INVENTION

Non-intrusive pressure measurement devices known from prior art comprise a proof body whose deformation is measured by means of a gage, called a strain gage, said proof body having to be mechanically coupled with the conduit so that the conduit's deformation, under the effect of the pressure of the fluid it carries, is transmitted to said proof body. International patent application WO2006122750 describes such a pressure sensor suitable for being implanted on an intracorporeal conduit such as a blood vessel. The need to obtain mechanical coupling between the conduit and the sensor's proof body locally modifies the conduit's mechanical response, even modifies the shape of this conduit, and can have consequences on the flow conditions of the fluid. Thus, such sensors do not allow a circumferential or axial pressure distribution to be measured over small distances.

OBJECT AND SUMMARY OF THE INVENTION

To remedy the deficiencies of prior art, the invention proposes a device for measuring the pressure of a fluid carried in a conduit, comprising:
a. a first electrode;
b. a second electrode;
c. an assembly of conductive or semi-conductive nanoparticles in contact with the two electrodes;
d. a measurement device providing proportional information with respect to an electrical property of the nanoassembly, which property is measured between the first and second electrode, said electrical property being sensitive to the distance between the nanoparticles of the assembly;
e. the nanoassembly, mechanically linked to a flexible substrate, having a mechanical linkage with the fluid carried by the conduit such that the distances between the nanoparticles of said assembly are modified by a pressure variation in said fluid.

Thus, the use of nanoparticles allows a sensor to be produced that is both very sensitive and of small size, adaptable to many measurement situations. In effect, placed in this way on a flexible substrate, said nanoassembly is able to be used as proof body and to directly measure a force applied to it, regardless of the rigidity of the mount on which the device is placed, or it can be bonded onto a proof body whose deformations it can measure; these two modes of use can be combined.

Other advantages of the use of nanoparticles will become apparent from advantageous embodiments, described below, which may be considered individually or in any technically effective combination.

Throughout the text, the verb "to link" and the term "linkage" express a functional relationship between two elements, more specifically the term "mechanical linkage" expresses a transmission of force between the elements in question, whether this transmission is direct or the force flow also traverses other elements.

Advantageously, the device that is the subject of the invention comprises means able to mechanically link the flexible substrate on which the nanoassembly is placed to the wall of a conduit carrying a fluid. This embodiment is especially advantageous for being able to temporarily bond the device that is the subject of the invention onto a conduit, for example on an intracorporeal conduit.

Advantageously, the flexible substrate is able to be linked to the conduit such that the nanoassembly is at the interface between said flexible substrate and a wall of the conduit. In particular, this configuration allows the nanoassembly to be retained as the pressure sensor's proof body, the substrate then having only a very limited effect on the fluid's flow conditions.

According to an embodiment of the device that is the subject of the invention, the means of mechanical linkage between the flexible substrate and the conduit comprise a ring able to be opened by a hinge to insert the conduit, the flexible substrate forming the hinge of this ring. This embodiment makes it possible to propose a measuring device in the form of a clip whose branches are rigid and easy to manipulate, without the branches' rigidity affecting the conduit's response, because of the flexibility of the hinge, but at the same time allowing precise measurement of variations, especially temporal, in the pressure of the fluid carried in said conduit.

Advantageously, the nanoparticles are made of gold and the flexible substrate is made of a bioresorbable material. In this way, the device that is the subject of the invention can be placed on an intracorporeal conduit and be eliminated naturally.

According to a particular embodiment of the device that is the subject of the invention, the electrical property measured by the nanoassembly is the electrical capacitance of this assembly. Thus, the variation in this electrical property, and thus in the pressure of the fluid carried in the conduit, can be measured without contact and remotely, in particular via a resonant circuit, without the nanoassembly being connected to a circuit by a wire connection. This embodiment is particularly advantageous when the device that is the subject of the invention is used to measure the pressure of a fluid carried in an intracorporeal conduit.

The invention also concerns an instrumented conduit able to carry a fluid and comprising a device according to any one of the embodiments described above.

According to an embodiment of this conduit, the measuring device is linked to the wall of the conduit, said conduit forming the proof body. This embodiment is especially suited to measuring the pressure of a fluid as it circulates in an extracorporeal conduit. The instrumented conduit is then simply placed in this circuit.

According to another embodiment, compatible with the previous one, the pressure measuring device is linked to the internal wall of the conduit in contact with the carried fluid. This embodiment is more specifically advantageous when the nanoassembly of the pressure measuring device is used directly as proof body. In this case, the instrumented conduit makes it possible to provide very precise information about the pressure distribution in the flow and from this deduce information about both the properties of the fluid and its flow conditions.

BRIEF DESCRIPTION OF THE DRAWINGS

The invention will now be described more precisely in the context of its preferred embodiments, which are in no way limiting, shown in FIGS. 1 to 6 wherein.

DETAILED DESCRIPTION OF THE EMBODIMENTS

Figure 1:
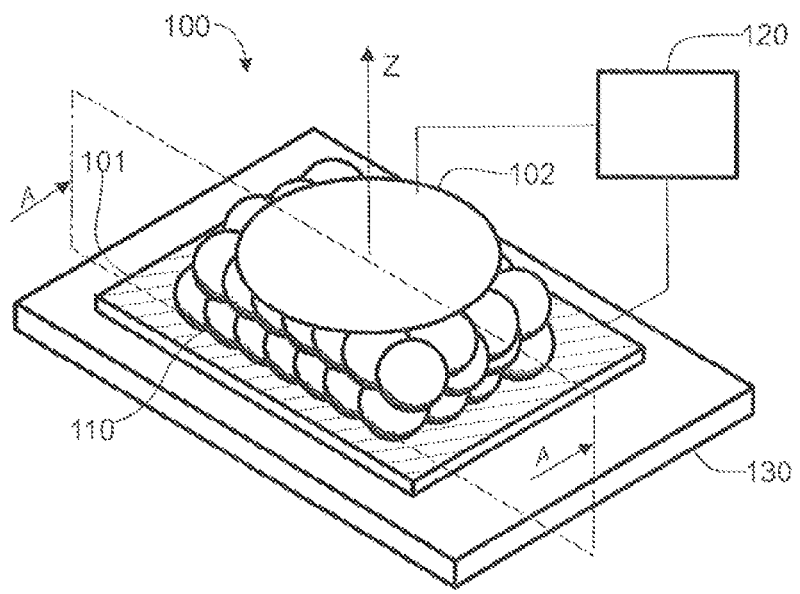
FIG. 1 represents, in perspective seen from the top, an elementary sensor forming part of the device that is the subject of the invention according to one of its embodiments.

FIG. 1: according to an exemplary embodiment, the measuring device that is the subject of the invention comprises an elementary sensor (100) comprising a first electrode (101) and a second electrode (102), an assembly of electrically conductive or semi-conductive nanoparticles (110) linked by an electrically insulating ligand (not shown). According to this embodiment, said assembly comprises at least two layers of nanoparticles (110) stacked according to a stacking direction (Z). The two electrodes (101, 102) are in electrical contact with the nanoassembly. Measurement means (120) allow an electrical property of the nanoassembly to be measured, for example its electrical resistance. The whole comprised of the two electrodes and the nanoassembly is placed on a substrate (130), and is advantageously covered by an insulating film (not shown). For the same deformation, such an elementary sensor is at least 100 times more sensitive than a conventional piezoresistive strain gage mounted in a bridge circuit, called a Wheatstone bridge. The dimension of the nanoparticles (110) is between $2 \cdot 10^{-9}$ meters, or nanometers, and can reach 50 μm, such that the elementary sensor is very thin, at most in the order of 0.2 mm, but can be reduced to 0.02 m ($10^{-6}$ meters) depending on the dimension of the nanoparticles and the number of stacked layers.

Figure 2:
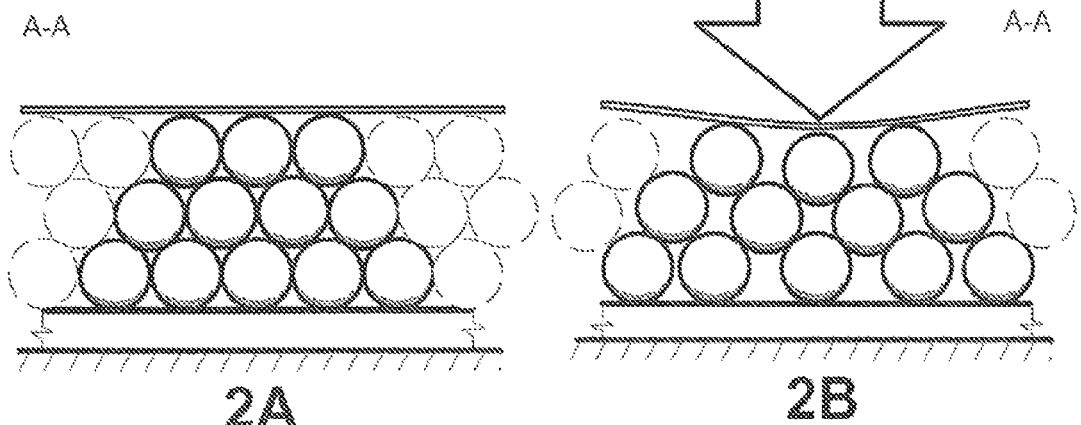
FIG. 2 shows, in cross-section, the operating principle of an elementary sensor according to an exemplary embodiment of the device according to the invention, where the elementary sensor is sensitive to a stress substantially parallel to the stacking direction of the nanoparticle layers, FIG. 2A with no stress on the elementary sensor, FIG. 2B where the elementary sensor is mechanically stressed.

FIG. 2A: view in cross-section with no stress, the nanoparticles of the elementary sensor assembly are organized according to a substantially compact stack. FIG. 2B: when a mechanical stress (200) is applied to the nanoassembly, the distance between all or some of the nanoparticles (110) of the assembly is changed, which changes said assembly's electrical properties. Measuring an electrical property sensitive to this distance thus allows the intensity of this mechanical stress to be determined. The mechanical stress can be a force, a pressure or a deformation imposed on the device that is the subject of the invention, either directly on it or via a proof body. The substrate (130) is called flexible because it does not oppose the change in the distance between the nanoparticles (110) when the assembly is directly subjected to stress.

Figure 3:
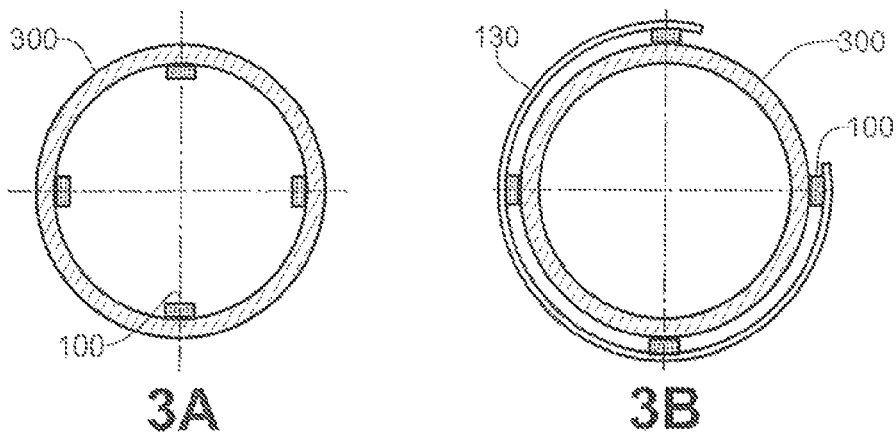
FIG. 3 shows, in cross-section and end-on, two variants of the implementation of a device that is the subject of the invention on a conduit, FIG. 3A on the internal wall of the conduit, FIG. 3B on the external wall of said conduit.

FIG. 3: according to exemplary embodiments of the device that is the subject of the invention, it comprises one or more elementary sensors (100), each comprising a nanoassembly, distributed over the circumference of a conduit (300), inside which a fluid is carried. Each of these elementary sensors operates according to the principle illustrated in FIG. 2, i.e. it is sensitive to a mechanical stress applied substantially parallel to the stacking direction of the assembly's nanoparticles.

FIG. 3A: according to an embodiment, the elementary sensors (100) are placed inside the conduit (300) in contact with the fluid carried. Thus, each of these sensors directly measures the pressure applied, where it is located. The elementary sensors (100) being very thin, their presence does not disrupt the flow in the fluid.

FIG. 3B: according to another embodiment, the elementary sensors (100) are placed outside the conduit (300), between the wall of said conduit and a substrate (130) of a shape substantially homothetic to the shape of the conduit. The elementary sensors' high sensitivity allows a substrate (130) to be used that has a rigidity substantially equivalent to that of the wall of the conduit (300) and its presence does not substantially change the flow conditions of the fluid in said conduit.

This flexible substrate (130) also allows the elementary sensors to be connected to the wall of the conduit (300), whether they are placed inside or outside said conduit. According to a first example of realization, the flexible substrate is essentially elastic and the connection with the conduit (300) is realized as a clip, by its expansion to connect it on the outside of the conduit or by contracting it to connect it on the inside of the conduit (300). Alternatively, the rigidity of the flexible substrate is low enough for it to be rolled around the conduit. In this last case, this connection can be completed by gluing.

Figure 4:
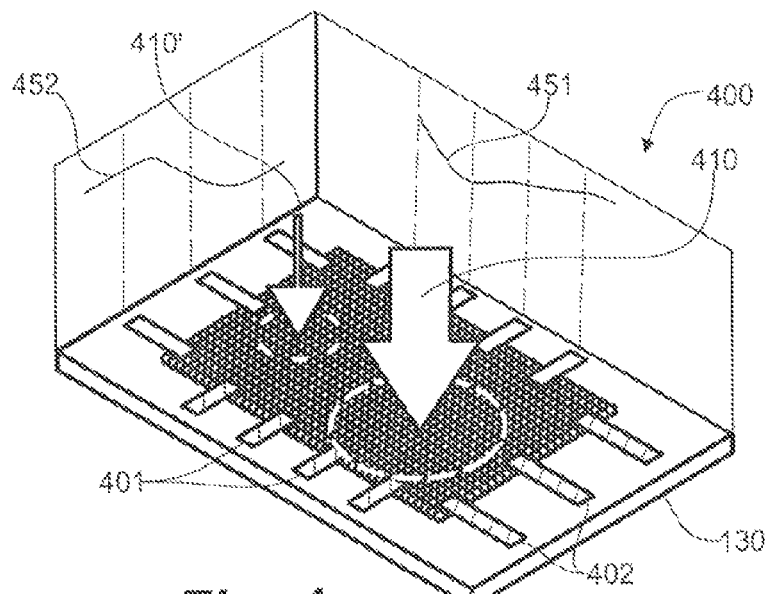
FIG. 4 shows the operation of an elementary sensor, called continuous, in perspective seen from the top.

FIG. 4: according to another example of realization of an elementary sensor, called an elementary continuous sensor (400), this comprises a plurality of first electrodes (401) and a plurality of second electrodes (402) in contact with a nanoassembly, deposited on a substrate (130). Thus, by measuring the variations in an electrical property of the nanoassembly when it is stressed by a system of stresses (410, 410'), and by performing a series of measurements in pairwise associations according to the various possible combinations of electrodes (401, 402) between these two pluralities, it is possible to establish a variation profile (451, 452) of said electrical property over the entire surface of the nanoassembly and, as a result, to deduce from this information about the system of stresses (410, 410') at the origin of this variation in the electrical property.

Figure 5:
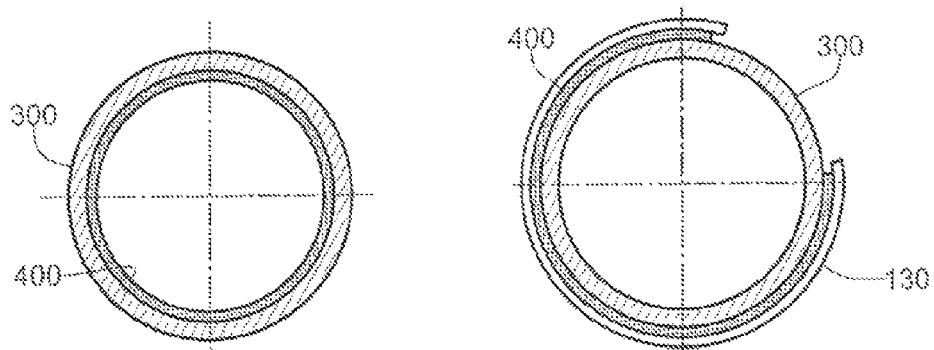
FIG. 5 is an example, seen end-on and in cross-section, of the use of an elementary continuous sensor as represented in FIG. 4, for realizing a device according to an embodiment of the invention, said elementary continuous sensor being installed inside a conduit, FIG. 5A, or outside the conduit, FIG. 5B.

FIG. 5: this elementary continuous sensor (400) can be used inside a conduit (300), FIG. 5A, or outside it, FIG. 5B, to obtain a map of the pressure of the fluid carried. FIG. 5A: according to an example of realization, the elementary continuous sensor (400) is deposited directly on the internal wall of the conduit, said conduit being made of a flexible material and playing the role of a substrate. The deposition can done using convective capillary deposition techniques, or using soft stamping lithography techniques. According to an example of realization, the deposition is realized flat, on the blank able to form the conduit, said blank then being rolled and welded to produce said conduit. Alternatively, the sensor can be deposited by soft lithography or by convective capillary deposition on the wall of the already rolled conduit, the latter being rolled up so as to expose its internal well to the outside.

FIG. 5B: according to another embodiment the elementary continuous sensor (400) is deposited on a substrate (130) of a shape homothetic to the conduit and then placed in contact with the external wall of said conduit (300). This embodiment is more specifically useful for placing said sensor on a conduit that cannot be opened, e.g. on an intra-corporeal conduit such as a vein. Such a sensor can thus be easily placed on this intra-corporeal conduit like a clip, with no trauma for said conduit. The great sensitivity of the elementary continuous sensor (400) allows to use a thin and flexible substrate (130), that does not disrupt the flow and can be left inside the body without causing any harm. For such intra-corporeal applications, the substrate can advantageously be made of a bioresorbable material, such as a lactic acid polymer or other bioresorbable polymers. The nanoparticles can advantageously be made of gold and deposited in a colloidal embodiment easily eliminated by the organism. With this type of nanoparticles, combined with non-toxic ligands and a bioresorbable substrate, the whole sensor (100, 400) is easily eliminated by the organism at the end of a defined period of time. Such a sensor can therefore be placed on an intracorporeal conduit so as to take measurements during a defined period of time without causing harm to the patient and be eliminated naturally without needing surgery for its removal.

Figure 6:
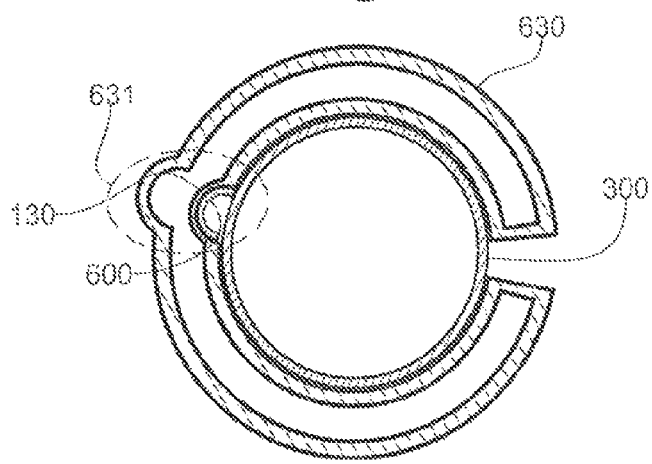
FIG. 6 represents, according to a cross-section end-on view, an exemplary embodiment of the device according to the invention utilizing a ring equipped with a hinge area.

FIG. 6: according to an embodiment variant, the device that is the subject of the invention comprises a proof body (630) able to be placed on a conduit (300) as a clip. This proof body (630) comprises a deformable hinge area (631) that is used as a substrate for an elementary sensor (600) comprising a nanoassembly. The proof body is in practice the hinge, a very flexible area, whose deformation is measured by the elementary sensor (600). For this type of application a single layer of nanoparticles is required, thus the sensor (600) can be extremely thin. The rigidity of the sensor outside the hinge area (631) allows it to be easily manipulated, for example to take measurements successively at various points of a conduit, especially intracorporeal. The elementary sensor, placed on the hinge (631), is protected from any degradation during this manipulation.

For convenience of representation, FIGS. 2 to 6 do not show the elementary conduit's wire connections to the measurement means (120). These connections can be, at least partially, realized in the substrate (130), by depositing them on the latter using lithography techniques or using micro- or nano-printing techniques, in particular utilizing electrically conductive inks.

According to a particular embodiment, the electrical property measured for the nanoassembly is the electrical capacitance of this assembly. Each pair of electrically conductive nanoparticles, separated by an electrically insulating ligand, forms a nano-capacitor, whose capacitance is a function, in particular, of the distance between said nanoparticles. The variation in capacitance between the electrodes (101, 102) is defined by placing all the capacitances between the nanoparticles of the assembly in series/in parallel. This configuration offers the possibility of being able to read the measurement remotely by means of protocols from the radiofrequency field, known from prior art. Thus, no wire connection with the sensor is required, which is particularly advantageous in the case of intracorporeal applications of said sensor, where this characteristic, combined with the device's capability for bioresorption, allows one or more devices according to the invention to be implanted on an intracorporeal conduit in order to take measurements and monitor these measurements over a given period of time, without causing harm to the patient.

Figure 7:
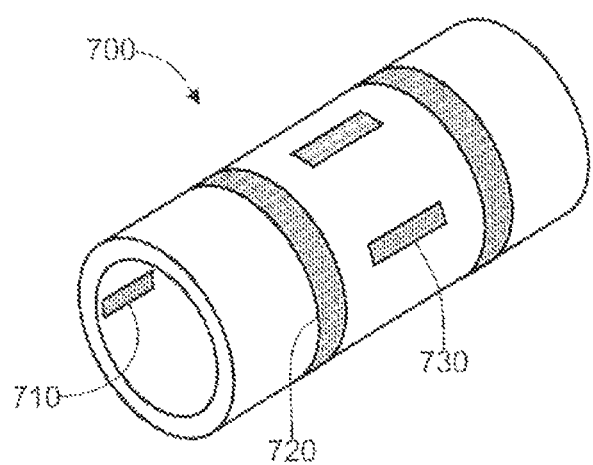
FIG. 7 is an exemplary embodiment, seen in perspective and end-on, of an instrumented conduit according to the invention.

FIG. 7: the invention also concerns an instrumented conduit (700) on which several elementary sensors are installed. These can be installed on the internal wall of the conduit (710) or on said conduit's external wall. The elementary sensors (710, 720, 730) can correspond to any one of the embodiments of the measuring device that is the subject of the invention and described above. As a non-limiting example, said instrumented conduit (700) can comprise, on its inner surface, one or more elementary sensors (710) directly sensitive to pressure. It can comprise, as an external wall, one or more elementary sensors (730) sensitive to the conduit's longitudinal deformation and one or more elementary sensors sensitive to the radial or circumferential deformation of the instrumented conduit (700). According to this embodiment, the elementary sensors (710, 720, 730) are adjusted to the characteristics of the conduit and combined so as to provide selected precise information either about the flow conditions of the fluid or about the properties of the fluid carried. Thus, the instrumented conduit can be inserted into a circuit in order to provide this information. The instrumented conduit (700) can advantageously be made of a bioresorbable material which, combined with elementary sensors (710, 720, 730) comprising suitable ligands and nanoparticles, allows said instrumented conduit to be inserted into an intracorporeal circulation circuit, being eliminated naturally later.

The above description clearly illustrates that through its various features and their advantages the present invention realizes the objectives it set itself. In particular, it allows a spatial and temporal distribution of pressure on a conduit, notably an intracorporeal circulation conduit of a fluid, to be measured. The sensor that is the subject of the invention does not require said conduit to be pierced in order to measure the internal pressure, thus avoiding any risk of effusion of the fluid carried as a result of the pressure measurement.

The invention claimed is:

1. A device for measuring the pressure of a fluid carried in a conduit, comprising:
   a first electrode;
   a second electrode;

a nanoassembly of conductive or semi-conductive nanoparticles in contact with the two electrodes;

a measurement device providing proportional information with respect to an electrical property of the nanoassembly, which property is measured between the first and second electrode, said electrical property being sensitive to the distance between the nanoparticles of the nanoassembly; and wherein the nanoassembly, mechanically linked to a flexible substrate has a mechanical linkage with the fluid carried in the conduit such that the distances between the nanoparticles of said assembly are modified by a pressure variation in said fluid.

2. The device according to claim 1, further comprising a proof body to mechanically link the flexible substrate on which the nanoassembly is placed to the wall of a conduit carrying a fluid.

3. The device according to claim 2, wherein the flexible substrate is linked to the conduit such that the nanoassembly is at the interface between said flexible substrate and a wall of the conduit.

4. The device according to claim 2, wherein the means of mechanical linkage between the flexible substrate and the conduit comprise a ring able to be opened by a hinge to insert the conduit, the flexible substrate forming part of the hinge of this ring.

5. The device according to claim 2, wherein the nanoparticles are made of gold and the flexible substrate is made of a bioresorbable material.

6. The device according to claim 1, wherein the electrical property is the electrical capacitance of the nanoassembly.

7. An instrumented conduit able to carry a fluid, comprising a measuring device according to claim 1.

8. A conduit according to claim 7, wherein the measuring device is linked to the wall of the conduit, said conduit forming a proof body.

9. A conduit according to claim 8, wherein the device is linked to the internal wall of the conduit in contact with the fluid carried.

* * * * *